United States Patent
Dillingham et al.

(10) Patent No.: US 10,380,754 B2
(45) Date of Patent: Aug. 13, 2019

(54) METHOD AND DEVICE FOR DETECTING SUBSTANCES ON SURFACES

(71) Applicant: Brighton Technologies LLC, Cincinnati, OH (US)

(72) Inventors: Raymond Giles Dillingham, Cincinnati, OH (US); Brietta Rose Oakley, Palmdale, CA (US); Lucas Hale Dillingham, Cincinnati, OH (US)

(73) Assignee: Brighton Technologies LLC, Cincinnati, OH (US)

(*) Notice: Subject to any disclaimer, the term of this patent is extended or adjusted under 35 U.S.C. 154(b) by 0 days.

(21) Appl. No.: 15/495,272

(22) Filed: Apr. 24, 2017

(65) Prior Publication Data

US 2017/0228882 A1    Aug. 10, 2017

Related U.S. Application Data

(63) Continuation-in-part of application No. PCT/US2015/057414, filed on Oct. 26, 2015.
(Continued)

(51) Int. Cl.
*G06T 7/60*     (2017.01)
*G01N 13/02*    (2006.01)
(Continued)

(52) U.S. Cl.
CPC .............. *G06T 7/60* (2013.01); *G01N 13/00* (2013.01); *G01N 13/02* (2013.01); *G01N 21/94* (2013.01);
(Continued)

(58) Field of Classification Search
CPC .... G06T 7/60; G06T 7/62; G06T 7/64; G01N 13/02; G01N 2013/0208; G01N 2021/945;
(Continued)

(56) References Cited

U.S. PATENT DOCUMENTS

| | | | | |
|---|---|---|---|---|
| 4,688,938 A | * | 8/1987 | Demoulin | G01N 13/02 356/138 |
| 5,115,677 A | * | 5/1992 | Martin | G01N 13/02 73/64.48 |

(Continued)

FOREIGN PATENT DOCUMENTS

| | | | | |
|---|---|---|---|---|
| EP | 1729109 A1 | * 12/2006 | ............. | G01B 11/26 |
| WO | WO-03036269 A1 | * 5/2003 | ............. | G01N 13/02 |

(Continued)

OTHER PUBLICATIONS

PCT/US15/57414—International Search Report and Written Opinion, dated Jan. 14, 2016, 3 pages.

*Primary Examiner* — James R Sheleheda
(74) *Attorney, Agent, or Firm* — Jenei LLC; Stephen R. Jenei (57) ABSTRACT

A testing device determines the presence of substances on a surface using a sensor positioned at a known vantage point to the surface. A liquid dispenser deposits a liquid drop on the surface. A data generator after a first time interval for allowing the liquid drop to stabilize on the surface detects, via the sensor, a geometric characteristic of the liquid drop that is related to a first equilibrium contact angle of the liquid drop to the surface. The data generator after a second time interval detects via the sensor the geometric characteristic of the liquid drop that is related to a second equilibrium contact angle. The data generator compares the first and second contact angle and determines a contamination on the surface that is soluble in the liquid drop in response to a change between the first and second contact angles.

23 Claims, 4 Drawing Sheets

Related U.S. Application Data (60) Provisional application No. 62/068,542, filed on Oct. 24, 2014.

(51) Int. Cl.
*G01N 21/94* (2006.01)
*G01N 13/00* (2006.01)
*G01B 11/02* (2006.01)
*G01B 11/08* (2006.01)
*G01B 11/24* (2006.01)

(52) U.S. Cl.
CPC .............. *G01B 11/02* (2013.01); *G01B 11/08* (2013.01); *G01B 11/24* (2013.01); *G01N 2013/0208* (2013.01); *G01N 2021/945* (2013.01)

(58) Field of Classification Search
CPC ........ G01N 13/00; G04N 21/94; G01B 11/02; G01B 11/08; G01B 11/24
See application file for complete search history.

(56) References Cited

U.S. PATENT DOCUMENTS

| | | | | |
|---|---|---|---|---|
| 5,137,352 A * | 8/1992 | Blitshteyn | ............... | G01N 13/02 356/138 |
| 5,143,744 A * | 9/1992 | Barth | ................ | B05C 5/02 118/319 |
| 5,268,733 A * | 12/1993 | Wright | ................ | G01B 11/26 356/138 |
| 5,583,285 A * | 12/1996 | Hahn | ................ | G01N 13/02 73/64.52 |
| 5,756,885 A | 5/1998 | Poku et al. | | |
| 5,798,455 A | 8/1998 | Sakata et al. | | |
| 5,838,445 A * | 11/1998 | Sandhu | ................ | G01B 13/22 356/600 |
| 5,861,946 A * | 1/1999 | Hudson | ................ | G01N 13/02 356/138 |
| 5,882,938 A * | 3/1999 | Takahashi | ............ | G01N 13/02 134/1 |
| 6,352,578 B1 * | 3/2002 | Sakata | ................ | B01D 53/02 55/385.2 |
| 6,765,662 B2 * | 7/2004 | Casati | ................ | G01N 13/02 356/150 |
| 7,155,962 B2 * | 1/2007 | Knebel | ................ | G01N 13/02 382/108 |
| 7,308,822 B2 * | 12/2007 | Sutton | ................ | G01N 13/02 73/104 |
| 9,534,132 B2 * | 1/2017 | Osako | ................ | C08K 5/5419 |
| 9,958,264 B2 * | 5/2018 | Williams | ............... | G01B 11/26 |
| 2006/0169032 A1 | 8/2006 | Sutton | | |
| 2008/0018909 A1 | 1/2008 | Osaka et al. | | |
| 2009/0133480 A1 * | 5/2009 | Ivanov | ................ | G01N 13/02 73/64.51 |
| 2009/0136654 A1 * | 5/2009 | Xu | ................ | B82Y 10/00 427/8 |
| 2009/0180106 A1 * | 7/2009 | Friedrich | ............... | G01N 13/02 356/138 |
| 2010/0024529 A1 | 2/2010 | Dillingham et al. | | |
| 2010/0069590 A1 * | 3/2010 | Utsumi | ................ | C07C 69/653 526/245 |
| 2011/0311764 A1 * | 12/2011 | Hulseman | ............... | B22F 3/17 428/131 |
| 2013/0135459 A1 * | 5/2013 | Hong | ................ | G01N 21/94 348/128 |
| 2013/0152668 A1 * | 6/2013 | Stukan | ................ | G01N 13/02 73/37 |
| 2014/0123854 A1 * | 5/2014 | Leonard | ................ | B03C 3/30 96/28 |
| 2014/0144518 A1 * | 5/2014 | Bohringer | ............ | B01L 3/50273 137/13 |
| 2015/0010731 A1 * | 1/2015 | Iwata | ................ | G02B 27/0006 428/141 |
| 2015/0076030 A1 * | 3/2015 | Smith | ................ | B65D 85/72 206/524.3 |
| 2015/0175814 A1 * | 6/2015 | Aizenberg | ............ | B08B 17/06 428/312.8 |
| 2015/0298157 A1 * | 10/2015 | Weitz | ................ | B06B 1/06 239/4 |
| 2015/0362417 A1 * | 12/2015 | Haberland | ............ | G01B 11/26 356/154 |
| 2016/0258882 A1 * | 9/2016 | Williams | ............... | G01B 11/26 |
| 2017/0101540 A1 * | 4/2017 | Tiang | ................ | C09D 5/1687 |
| 2017/0146461 A1 * | 5/2017 | Vahey | ................ | G01N 21/94 |
| 2017/0227683 A1 * | 8/2017 | Hervieu | ............... | G02B 1/10 |
| 2017/0307536 A1 * | 10/2017 | Dillingham | ........... | G01N 13/02 |
| 2017/0313728 A1 * | 11/2017 | Sakurai | ................ | C08G 79/00 |
| 2017/0313902 A1 * | 11/2017 | Shimazaki | ............... | C09D 7/20 |

FOREIGN PATENT DOCUMENTS

| | | | | |
|---|---|---|---|---|
| WO | 2012140338 A1 | 10/2012 | | |
| WO | WO-2016065366 A1 * | 4/2016 | ............ | G01N 13/02 |

* cited by examiner

METHOD AND DEVICE FOR DETECTING SUBSTANCES ON SURFACES

CROSS-REFERENCE TO RELATED APPLICATIONS

This application is a continuation-in-part application filed under 35 U.S.C. § 111(a) and claims priority to the Patent Cooperation Treaty Application No. PCT/US15/57414, entitled "Method And Device For Detecting Substances On Surfaces" filed Oct. 26, 2015, which in turn claims the benefit of priority to U.S. Patent Application Provisional Application Ser. No. 62/068,542 entitled "Method And Device For Detecting Substances On Surfaces", filed 24 Oct. 2014, the disclosures of which are incorporated herein by reference in their entirety.

BACKGROUND OF THE INVENTION

1. Field of the Invention

The field of art disclosed herein pertains generally relates to a device and method for detecting substances on a surface.

2. Description of the Related Art

A need exists for a method and a device that is quickly and quantitatively sensitive to the properties of the surface of a material or an object. One reason for making these measurements is to determine if a surface is properly prepared and ready for further processing, such as printing, bonding, or sealing. Another reason is to determine if a cleaning process is working correctly to remove contaminants from a surface. Another reason is to provide a feedback signal that can be used to control a process such as a coating process or a corona, flame, or plasma treatment process.

One technique for measuring the properties of a surface involves observing the behavior of drop of liquid placed onto the surface. When a drop of liquid is deposited onto a surface and allowed to come to equilibrium, it forms a shape determined by the balance of several forces: the liquid surface tension, the solid surface energy, the gravitational force on the liquid, and the strength of attraction between the liquid and the surface on which it rests. The shape of the drop is defined by the contact angle θ. This is the angle between the surface and a tangent to the drop at the point of intersection of the drop with the surface. A small contact angle is observed when the liquid spreads on the surface, while a large contact angle is observed when the liquid beads on the surface. More specifically, a contact angle less than 90° indicates that wetting of the surface is favorable, and the fluid will spread over a large area on the surface; while contact angles greater than 90° generally means that wetting of the surface is unfavorable so the fluid will minimize its contact with the surface and form a compact liquid droplet.

Figure 1:
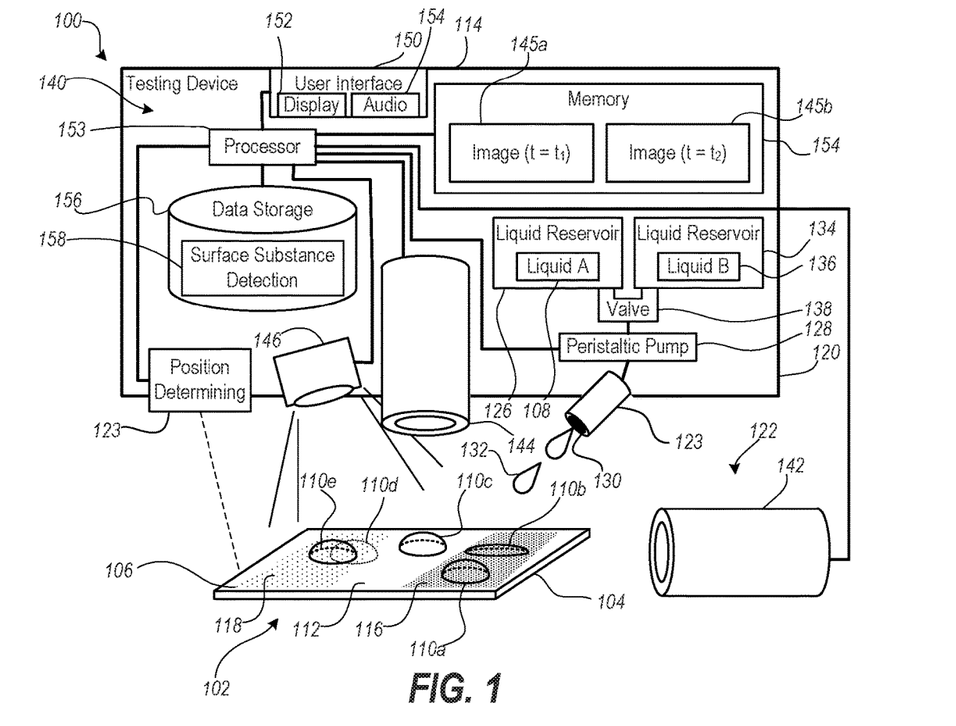
FIG. 1 illustrates a block diagram of a testing device for depositing a liquid drop and determining the contact angle as a function of time in order to determine presence of a contaminant on a surface, according to one or more embodiments.

FIG. 1 illustrates a diagram of a small liquid drop on a surface. The dashed line represents a circle with the same radius of curvature R as the spherical drop. Angle θ is the contact angle, d is the diameter of the contact patch, h is the maximum height of the drop above the surface, and A is the maximum cross-sectional area of the drop.

The relationship of the contact angle to the surface tension of the liquid and the substrate surface energy is defined by the Young equation:

$$\gamma_s = \gamma_{sl} + \gamma_l \cos\theta \quad (1)$$

Where $\gamma_s$=substrate surface energy
$\gamma_{sl}$=substrate-liquid interfacial energy
$\gamma_s$=liquid surface tension Contact angles are usually measured using a device known as a contact angle goniometer. A drop of the probe liquid is placed on the surface to be interrogated, the plane of the surface is brought into the line of sight of a telescope containing a measuring scale, and a reticle in the telescope is made tangent to the drop profile at the point of contact with the surface. The angle that this line makes with the surface is defined as the contact angle. In one or more embodiments, the contact angle can also be determined by computerized analysis of a digital image of the drop.

A contact angle does not have to be directly measured. Small drops (typically less than about 10 microliters) form a spherical shape. The contact angles in these cases can be calculated from other geometrical features of the drop, such as the diameter of the contact patch, the radius of curvature, the height, or the cross sectional area, and the volume. For larger drops that are no longer spherical, the contact angle can be approximated quite precisely through the use of more complex equations.

Generally, if the water contact angle is smaller than 90°, the solid surface is considered hydrophilic and if the water contact angle is larger than 90°, the solid surface is considered hydrophobic. Many polymers exhibit hydrophobic surfaces. Highly hydrophobic surfaces made of low surface energy (e.g. fluorinated) materials may have water contact angles as high as ~120°. Some materials with highly rough surfaces may have a water contact angle even greater than 150°, due to the presence of air pockets under the liquid drop. These are called superhydrophobic surfaces. If the liquid molecules are strongly attracted to the solid molecules then the liquid drop will completely spread out on the solid surface, corresponding to a contact angle of 0°. This is often the case for water on bare metallic or ceramic surfaces.

Because the contact angle is determined by the interaction of the liquid with the uppermost few molecular layers of the surface, the presence of an oxide layer or of some other substance on the solid surface can significantly change the contact angle. Hydrophobic substances tend to increase the contact angle of water, while hydrophilic substances tend to decrease the water contact angle. Less than a monomolecular layer of some substances can change the contact angle by several degrees, a readily measurable amount. This makes contact angle measurements especially useful for detecting the presence of contaminants or other substances on a surface. Furthermore, one can establish a quantitative relationship between the amount of a substance on a surface and the contact angle established with a particular liquid, making contact angle measurements useful for quantifying the amount of substance on a surface in some instances.

The use of contact angle measurements to confirm the existence of a certain surface composition can be hampered by the presence of substances on the surface that can interact with the liquid, for example through dissolution or chemical reaction. This interaction will change the properties of the surface and the liquid and can affect the contact angle. An example is the presence of a hydrophilic substance such as a surfactant on a metal or ceramic surface. When drop of a liquid such as water is placed on a surface that has surfactant on it, the surfactant will tend to dissolve into the water. This removes the surfactant from the surface, increasing its surface energy, while simultaneously decreasing the surface tension of the water. The combination results in a low contact angle. This low contact angle can be confused with the low contact angle presented by a clean metal or ceramic surface. Because of the possibility of confusing a clean surface with a surface having a soluble or reactive substance on it, contact angle measurements have not been widely used for confirming surface properties. Consequently, a need exists for an improved system and method of detecting a contact angle that accounts for the presence of soluble or reactive substances on the surface.

SUMMARY OF THE INVENTION

The present innovation relates generally to a device and method for detecting substances on a surface. In one or more embodiments, a testing device determines the presence of substances on a surface using a sensor positioned at a known vantage point to the surface. A liquid dispenser deposits one or more liquid drops on the surface. Alternatively, liquid could be deposited onto the surface via condensation from vapor. In one or more embodiments, the liquid dispenser deposits one or more liquid drops on the surface as a continuous stream. A data generator after a first time interval for allowing the liquid drop to stabilize on the surface detects via the sensor a geometric characteristic of the liquid drop such as contact angle, diameter, contact angle, height, radius of curvature, or contact area that is related to an initial contact angle of the liquid drop(s) to the surface. The data generator after a second time interval detects via the sensor the geometric characteristic of the liquid drop that is related to a second contact angle. The data generator compares the first and second geometric characteristics and determines a difference (if any) between the first and second geometric characteristics. The presence of a substance on the surface that is either soluble in the liquid drop or capable of a chemical interaction with the liquid drop will result on a change between the first and second geometric characteristics. This change is an indicator of the presence of such a substance on the surface. The magnitude and/or rapidity of the change is indicative of the type and amount of substance on the surface.

According to one or more embodiments, the present innovation provides a method of determining the presence of substances on a surface. The method includes depositing a liquid drop on a surface. After a first time interval for allowing the liquid drop to stabilize on the surface, the method includes detecting a geometric characteristic of the liquid drop that is related to a first equilibrium contact angle of the liquid drop to the surface. After a second time interval, the method includes detecting the geometric characteristic of the liquid drop that is related to a second equilibrium contact angle of the liquid drop to the surface. The method further includes comparing the first and second geometric characteristics; and determining the presence of a substance on the surface that is soluble in the liquid drop or capable of a chemical interaction with the liquid drop in response to a change between the first and second geometric characteristics.

According to one or more embodiments, the present innovation provides a method of determining the presence of substances on a surface. The method includes depositing a liquid drop on a surface. The method includes detecting one or more initial geometrical characteristics of the drop, such as contact angle, diameter, contact angle, height, radius of curvature, or contact area. The method includes detecting a change in the geometrical characteristic of the drop, such as diameter, contact angle, height, radius of curvature, or contact area, after an elapsed time chosen so as to allow the liquid drop to interact with any substance present on the surface. The method includes comparing the amount of change in the geometrical characteristic to a threshold amount that is preset based upon characteristics of a known clean surface. The method includes determining the surface to have a substance on it in response to the comparison to the threshold amount.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

The present innovation relates generally to a device and method for detecting substances on a surface. In one embodiment, the present invention provides for a device and method for determining a geometrical characteristic (feature) of a liquid in contact with a surface. In another embodiment, the present innovation provides for devices and methods for determining the presence of substances or contaminants on a surface by determining changes to one or more geometrical feature of a liquid in contact with a surface.

FIG. 1 illustrates a testing system 100 for detecting substances or contaminants 102 on a surface 104 of a test article 106. In particular, the testing system 100 detects the presence of substances or contaminants 102 on the surface 104 by determining changes to one or more geometrical features of a liquid 108 in contact with the surface 104. As a control, a drop 110a of liquid 108 is placed on a known clean surface, which for clarity is shown as a central portion 112 of the surface 104 of the test article 106. An equilibrium contact angle (or other geometrical characteristic related to the contact angle, such as diameter, height, radius of curvature, or contact area) is established and measured by a testing device 114 of the testing system 100. In a first scenario, the surface 104 includes a contaminant 102 that is a layer 116 that is soluble to the liquid 108. The geometrical characteristic that changes over one or more time intervals and is measured, depicted as an initial drop 110b having a greater contact angle than a subsequent drop 110c. The determination of changes to geometrical characteristics with time indicates the presence of a substance or contaminant on the surface 104 that is interacting with the liquid 108 to either change the surface tension of the liquid 108 or the surface energy of the surface or both. In a second scenario, the surface 104 includes a contaminant 102 that is a layer 118 that has a different adherence characteristic than the clean surface and can be insoluble to the liquid 108. With horizontal energy imparted to an initial drop 110d on the layer 118, such as by horizontal momentum, surface vibration, or an inclination to the surface 104, the initial drop 110d can translate to a subsequent drop 110e that is more or less than the translation of the drop 110a on the clean surface.

In one embodiment, the testing device 114 is incorporated within a housing 120 that positions a sensor 122 at a known vantage point to the surface 104, such as determined by a physical structure or a position determining component 123. A liquid dispenser 124 deposits the liquid drops 110a-110e on the surface 104. For example, the liquid 108 can be contained in a liquid reservoir 126 that is propelled by a peristaltic pump 128 through an orifice 130 of the liquid dispenser 124 that is sized to create droplets 132 of a selected volume and at a selected velocity. In one embodiment, a second liquid reservoir 134 contains a second liquid 136 having a wetting characteristic or different solubility characteristic in order to obtain a more accurate measurement of any contaminants 102. A valve 138 is switched between the liquid reservoirs 126, 134. Thus, contact angle measurements can be determined with two or three liquids in order to evaluate these two- or three component vector quantities and to obtain a more accurate surface energy calculation.

Exemplary liquids that may be used with the device and method described here are deionized water, dimethyl sulfoxide (DMSO), methylene iodide, hexane, mixtures of formamide with glycol monoethyl ether, alcohols such as ethanol, mixtures of water and ethanol, and other liquids with desirable wetting characteristics.

A data generator 140 of the testing device 114, after a first time interval for allowing the liquid drop 110a-110e to stabilize on the surface 104, detects via the sensor 122 a geometric characteristic of the liquid drop 110a-110e that is related to a first contact angle of the liquid drop to the surface 104. After a second time interval, the data generator 140 detects via the sensor 122 the geometric characteristic of the liquid drop 110a-110e that is related to a second contact angle of the liquid drop to the surface 104. The data generator 140 compares the first and second contact angle and determines a substance 102 on the surface 104 that is either soluble in the liquid drop or capable of reacting with it in some way 110a-110e in response to a change between the first and second contact angles.

In one embodiment, the data generator 140 detects via the sensor 122, which includes a goniometer telescope 142, the geometric characteristic of the liquid drop 110a-110e by viewing with the telescope 142 the liquid drop 110a-110e from side superimposed against contact angle marks around perimeter. The data generator 140 measures visually the tangent of the liquid drop 110a-110e to the surface 104.

Alternatively or in addition, the sensor 122 can include a video camera 144 that is positioned to measure one or more parameters of the volume, height, base diameter, and curvature of the liquid drop 110a-110e. The data generator 140 analyzes images 145a, 145b of the liquid drop 110a-110e to measure two or more parameters selected from the group consisting of volume, height, base diameter and curvature of the liquid drop 110a-110e. In one embodiment, the volume of the liquid drop 110a-110e is known based upon the repeatability of the creation of droplets 132. Based upon the analysis, the data generator 140 calculates a contact angle based upon the two or more parameters.

In one embodiment, the testing device 114 further includes an illuminator 146 such as a laser. The data generator 140 detects via the sensor 122 the geometric characteristic of the liquid drop by illuminating the liquid drop 110a-110e with the illuminator 146. The data generator 140 measures one of reflection and refraction imparted to the illumination by the liquid drop 110a-110e. The data generator 140 determines the contact angle based upon the measured one of reflection and refraction.

In addition, the sensor 122 can include a laser and a detector to sense a reflected beam, an ultrasonic transducer and receiver, and/or a fluorescence or absorption detector to establish a geometric characteristic of the drop.

In another embodiment, the components are incorporated into a single device that would be extremely convenient for use in a manufacturing environment on a variety surfaces and structures in a variety of orientations.

In one aspect of the invention, the liquid dispenser involves the ballistic deposition of multiple smaller volumes of liquid to the surface of the material to construct the volume of liquid. This embodiment includes a nozzle in fluid communication with a liquid reservoir. The liquid is pressurized prior to exiting the nozzle and may be pressurized in the reservoir, the nozzle, or in an intermediate stage, such as in a peristaltic pump. Pressurization of the liquid reservoir may be accomplished by a piston or by other pressurization techniques, such as pumps and gas charging. The nozzle may be electrically actuated between an open state and a closed state such that when in the open state the pressurized liquid is dispensed onto the surface of the material through the nozzle, and when in the closed state liquid is not dispensed. This embodiment dispenses pulses of multiple smaller volumes of liquid directed to the same location of the surface of the material to construct the volume of liquid. For example, eighteen (18) 83 nl droplets form 1.5 ul final droplet. However, this can be deposited as one large drop or at least 1, 2, 3, 4, 5 10, 15, 20, 25, 30 or more micro-droplets.

The smaller volumes of liquid may be on the order of about 10 nl, about 50 nl, about 100 nl, about 200 nl, about 300 nl, or about 400 nl. The smaller volumes are provided in pulses to reach the final volume of liquid, which, in one embodiment, may range from between about 0.5 µl to about 10 µl. In another embodiment, the final volume of liquid may range from between about 1 µl to about 5 µl. In another embodiment, the final volume of liquid is about 2 µl. The volume of liquid may be deposited over a relatively short period of time ranging from about 0.01 seconds to about 1.0 seconds. In one embodiment, the volume of liquid is deposited in about 0.5 seconds or less. Other smaller volumes of liquid and final volumes of liquid, and deposition times may also be used in the presently described devices and methods. For example, a nozzle releases droplets through pulses by holding open for about 1.4 ms per pulse; these occur at a frequency of about 143 Hz and create the total drops in 18 pulses.

In another embodiment, the liquid dispensing component is an elongated hollow projection having an opening distal to the housing 120 and a fluid reservoir in fluid communication with the hollow projection. Examples of possible elongated hollow projections include syringe needles and pipette tips. The volume of liquid passes from the fluid reservoir, through the hollow projection, and exits the hollow projection at the distal opening where it is deposited onto the surface of the material.

The elongated hollow projection may optionally double as a kinetic energy imparting component. For example, the hollow projection may be coupled to a device capable of imparting kinetic energy in the form of vibration to the hollow projection, which in turn imparts the kinetic energy to the volume of liquid. Examples of suitable kinetic energy imparting devices are an electromagnetic transducer, a piezoelectric transducer, an electric motor with an eccentric mass, an acoustical device, and combinations of these devices.

The position determining component determines the position of the device relative to the volume of liquid on the surface by measuring at least one of the distance of the data generating component from the surface of the material or the angle of the data generating component relative to the surface of the material. The position determining component may be as simple as a mechanical probe having a fixed length which maintains a fixed distance between the data gathering component and the volume of liquid on the surface. In this embodiment, the mechanical probe contacts the surface of the material to maintain the relative position of data generating component. The position determining component may also include a point light source, a laser, and an acoustical measuring device (not shown).

The use of a point light source, laser, or acoustical measuring device as the position determining component, may allow the device to accurately measure or calculate the contact angles without actually contacting the surface of the material. The point light source illuminates an area on the surface of the material. The shape of the illuminated area will be a conic section. The shape of the illuminated area may be analyzed along with the volume of liquid to calculate the distance from the surface and the angle (alpha) between the plane of the surface and the data gathering component. The point light source, laser, and acoustical measuring device allow for the construction of a device which merely has to be pointed at the surface from anywhere within a range of distances, such as within a range of about 0.1, 0.2, 0.3, 0.4, 0.5 inches to about 1, 2, 3 inches or more, or in a range of about 1 inch to about 1.5 inches. The range of distances over which the device may operate is determined by various factors including, for example, the effective ranges of operation for the liquid dispensing component and/or the data generating component.

The data generating component is a device capable of obtaining information about the geometry of the volume of liquid on the surface of the material. The geometric information includes the shape, the contact angle of the lead edge, average contact angle, drop diameter (d), drop height (h), drop volume (v), the average diameter, and/or the curvature of the volume of liquid on the surface of the material. Exemplary data generating components include a camera, laser, scanner, and/or an acoustical device. The exemplary data generating component illustrated in the figures is a camera. In some embodiments, the data generating component and the position determining component can be included in the same element. For example, a laser or an acoustical device could function as both a data generating component and the position determining component.

The device may also include an additional source of illumination such as a light emitting diode (LED), laser, fluorescent, incandescent, strobe light, camera flash, or other suitable source of light for illuminating the volume of liquid on the surface of the material. The source of illumination may be incorporated into the housing 120 or may be separate from the housing 120.

The testing device 114 may be operated by a single actuating device, or, where desired, additional actuating devices or user interfaces 150 including a visual display 151 and auditory signaling device 152 could be added to control the device or to input data, such sample information or test parameters. The user interface 150 could include a touch screen, a keypad, a toggle, a button, a rollerball, a wheel, a dial, a mouse, etc. The testing device 114 may include a microprocessor 153 and may optionally entirely contained within the housing 120. The testing device 114 could utilize memory 154 a storage device 156 can store data collected and generated by the testing device 114. The data generator 140 can include a surface substance detection utility 158 that is stored in the storage device 156 and executed by the microprocessor 153. The stored data could be retrieved from the device by known methods, such as wireless transmission to a remote device, storage on removable media (not shown), like a thumb drive or memory chip, and transmission via an electric cable or docking station (not shown). The stored data could have numerous uses such as with quality control and compliance with manufacturing standards and regulations.

The display may include a light emitting diode (which includes both individual and screens of light emitting diodes), a liquid crystal display, and/or a gauge. The display 151 may be located in or on the housing 120 or, may be located in or on a secondary housing or remote device, and coupled to at least a portion of the testing device 114 by at least one of an electrical contact, electrical cable, and a wireless connection. The display 151 can convey any information deemed relevant to the use of the device such as the surface energy of the surface, a representation of the volume of the liquid on the surface, an image of the volume of the liquid on the surface, a pass indicator, a fail indicator, an error message, a diameter of the volume of the liquid on the surface, an average diameter of the volume of the liquid on the surface, the contact angle formed by the volume of liquid on the surface, the shape of the volume of liquid on the surface, the wetting characteristics of the surface, battery charge, and reservoir volume.

The device may optionally include an auditory signaling device 152. The auditory signaling device may be as simple a tone or mixture of tones, or complex as speech. The auditory signaling device may, for example, indicate that the device is in use, that a test was successfully or unsuccessfully completed, a pass or fail indicator, an error, that the testing device 114 is the correct relative position relative to the surface, battery life, and remaining liquid volume in the reservoir.

Figure 2:
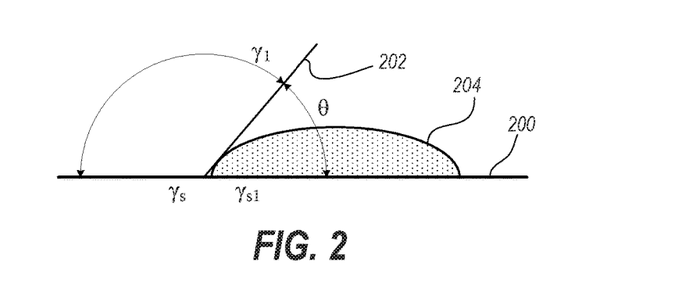
FIG. 2 illustrates a graphical depiction of a contact angle is the angle between the surface and a tangent to the liquid drop at the point of contact with the surface that is determined by the testing device of FIG. 1, according to one or more embodiments.

The properties of a surface are determined primarily by the surface chemical composition. One measurable property that is sensitive to the surface chemical composition is the contact angle established between a liquid drop and the surface. In FIG. 2, the contact angle theta $\theta$ is the angle between a surface 200 and a tangent 202 to a liquid drop 204 at the point of contact with the surface 200. The contact angle theta $\theta$ can be determined by three parameters: the surface energy of the surface ($\gamma_s$), the surface energy of the liquid ($\gamma_l$), and the interfacial energy between the liquid and the surface ($\gamma_{sl}$), and is described by the Young Equation:

$$\cos\theta = \frac{\gamma_s - \gamma_{sl}}{\gamma_l} \quad (1)$$

Both $\gamma_s$ and $\gamma_{sl}$ are sensitive to the surface chemical composition and therefore the contact angle $\theta$ is sensitive to the surface composition. Because of the geometry of a liquid drop, there are other features that can be measured instead of or along with the contact angle. These include the diameter ($D_1$) and/or the height ($h_1$) of the drop, which can be used to calculate the contact angle by a variety of methods.

Contact angles are convenient and fast to obtain and are extremely sensitive to small changes in surface composition. However, in some instances it is possible to obtain the same contact angle for surfaces of two different chemical compositions. For example, a metal surface that is contaminated with a thin film of oil or other soils will show a contact angle of perhaps 60°. This is because $\gamma_s$ is low for a contaminated surface while $\gamma_l$ is high for water. With reference to Equation 1, cos $\theta$ will be small and therefore $\theta$ will be large. If this surface is cleaned, $\gamma_s$ increases and $\theta$ will be small. This is because $\gamma_s$ is high for clean metal surfaces. Contact angles for water on clean metal surfaces can be 10° or less.

However, if a metal surface is contaminated with a thin film of dried detergent, for example from a washing process with an incomplete rinsing step, it can also show a low contact angle of around 10°. This results from the liquid dissolving a small amount of the detergent, which has two effects. It reduces the surface tension of the water ($\gamma_l$), which increases cos $\theta$ and lowers $\theta$. It also increases the surface energy of the substrate ($\gamma_s$) because it is removing the low surface tension contaminant. This also increases cos $\theta$ and lowers $\theta$. This means that there are circumstances where a contact angle measurement could result in the erroneous conclusion that a surface is clean whereas it is actually contaminated with an undesirable substance.

There is a need for a device and a method that can distinguish between a surface that establishes a low contact angle with a liquid because it is clean, and a surface that establishes a low contact angle with a liquid because it is contaminated with a surface active agent such as a detergent or surfactant.

In one embodiment, the present invention provides for a device and method for determining a geometrical feature of a liquid in contact with a surface. In another embodiment, the present invention provides for devices and methods for determining the presence of substances or contaminants on a surface by determining changes to one or more geometrical feature of a liquid in contact with a surface. In one embodiment, the present invention provides for a device and method for determining a geometrical feature of a liquid in contact with a surface. In another embodiment, the present invention provides for devices and methods for determining the presence of substances or contaminants on a surface by determining changes to one or more geometrical feature of a liquid in contact with a surface.

The present innovation provides for methods for determining the presence of substances or contaminants on a surface by determining changes to one or more geometrical features of a liquid in contact with a surface wherein a drop of liquid is placed on a clean surface. An equilibrium contact angle is established. Then the changes in the contact angle (or geometrical feature related to contact angle) over one or more time intervals are measured. Determination of changes to contact angle (or related geometrical feature) with time indicates the presence of a substance or contaminant on the surface that is interacting with the liquid to either change the surface tension of the water or the surface energy of the substrate or both.

In one embodiment, the placement of a droplet of liquid on a surface having a small amount of a soluble contaminant on it, the contact angle changes with time as the contaminant is dissolved. The time required for measurement of the contact angle changes depends on such factors as the viscosity of the liquid and time for dissipation of any vibrations from kinetic energy. Generally, it is not possible to deposit a droplet of liquid without imparting at least some kinetic energy (KE). Generally, the methods of the present invention require approximately 0.1-0.3 seconds for the droplet to reach a stable place then measurements can be made over time. Measurement time can be as little as about 1/millionth of a second to around 0.1 s to several seconds.

In one embodiment, the measurement time is at least 0.1, 0.2, 0.3, 0.4, 0.5, 1.0, 1.5, 2.0, 2.5, 3.0 seconds or longer. In one embodiment, the detection of the presence of these contaminants on the surface is accomplished by measuring the contact angle immediately after deposition of the liquid drop and then a various time intervals. In another embodiment, no change in contact angle with time indicates the surface does not have a soluble or reactive contaminant. If, however, the contact angle evolves with a time scale greater than that of a normally expected clean surface, it can be assumed that the surface properties are evolving with time and there is a substance or contaminant present on the surface that is interacting with the liquid to either change the surface tension of the water or the surface energy of the substrate or both.

The contact angle theta ($\theta$) is the fundamental parameter that can be calculated from various combinations of two or more parameters selected from the group consisting of volume, height, base diameter, cross sectional area, and curvature of the liquid drop. The drop geometry evaluating component that determines the above parameters is a data generating component for depositing a liquid drop and determining the contact angle as a function of time. In one or more embodiments, the testing device can measure parameters that correlate with a parameter closely related to surface energy as an indirect method of calculating contact angle.

For example, if uses a device that deposits a known volume and determines the resulting drop diameter, these parameters provide enough information that one could calculate contact angle. However, the methods do not require calculating the contact angle. All that is needed is the information for enough parameters related to the contact angle. The present invention is not dependent upon how the measurement is taken, just that parameters are measured such that one can measure the change in contact angle, directly or indirectly, as a function of time after drop deposition.

In one embodiment, analysis of contact angle can include one or more of:
1. Put drop on stage, view from side with telescope, see inverted surface, line up, angle marks around perimeter; measure visually the tangent of the drop to the surface;
2. Use video analysis, from various combinations of two or more parameters selected from the group consisting of volume, height, base diameter and curvature of the liquid drop;
3. Shine an illuminator [e.g., a light beam or laser] on droplet and measure reflection/refraction angle [e.g., by using CCD];

4. Position determining component; and
5. Perform drop analysis.

In one embodiment, the placement of a droplet of liquid on a surface having a small amount of a soluble substance on it, the contact angle changes with time as the substance is dissolved. The time required for measurement is at least 0.1, 0.2, 0.3, 0.4, 0.5, 0.6, 0.7, 0.8, 0.9, 1.0, 1.5, 2.0, 2.5, 3.0 seconds or longer. In one embodiment, the detection of the presence of these contaminants on the surface is accomplished by measuring the contact angle immediately after deposition of the liquid drop and then at various time intervals. In another embodiment, no change in contact angle with time indicates the surface does not have a soluble contaminant. If, however, the contact angle evolves with time, it can be assumed that the surface is evolving with time and there is a substance present on the surface that is interacting with the liquid to either change the surface tension of the water or the surface energy of the substrate or both.

The presence of other types of contaminants also result in time-dependent behavior, and by measuring the time-dependent nature of the liquid-surface interaction, information is obtained about the surface that can allow the type of contaminant to be determined. For example, if a film of a partly or wholly insoluble liquid is present on a surface, and a drop of liquid is deposited on the surface in a manner that imparts some energy to the liquid drop that includes a component parallel to the surface, the drop will exhibit horizontal displacement after deposition.

Obtaining more than one measurement can be by imaging methods but can be any measurement of properties correlating to contact angle. For example, an image of the drop during or immediately after it is deposited onto the surface reveals this displacement and is a positive indicator that the surface is covered with a liquid film. In one example, a thin film of a lubricating oil is present on a metal surface, and a drop of liquid is deposited onto this film-covered surface such that it contains some kinetic energy (due to vibration, for example) or potential energy (due to inclination of the surface, for example). In one embodiment, sequential images obtained during and after deposition of the liquid drop reveal horizontal displacement and indicate to an operator that a liquid film is present on the surface. Such knowledge is valuable for automatically detecting the presence of substances on the surface, for example an oil film on a machined metal component immediately prior to a painting operation.

In one or more embodiments, the sensor 122 may be an imaging sensor. In other embodiments, the measurement sensing may be by reflecting a laser off the surface of the liquid and onto a position sensitive detector to measure the height of a point on the droplet.

After depositing a liquid drop, multiple images are obtained and can be compared either with one another or with a predetermined table of values to determine if the drop is reducing in contact angle (growing in diameter) or if it is stable, and if it is displacing in the plane of the surface. If the drop shape is stable, then the absence of a soluble contaminant can be assumed. If the drop shape is evolving with time, then the presence of a soluble contaminant that alters the surface tension of the liquid and surface can be presumed. If the drop displaces horizontally either during and/or immediately after deposition, then the presence of a liquid film that is either partially or wholly insoluble in the liquid drop can be presumed. Combined with other knowledge about the environment and history of the surface, this information provides important information about the chemical nature of any contaminants present on the surface.

Figure 3:
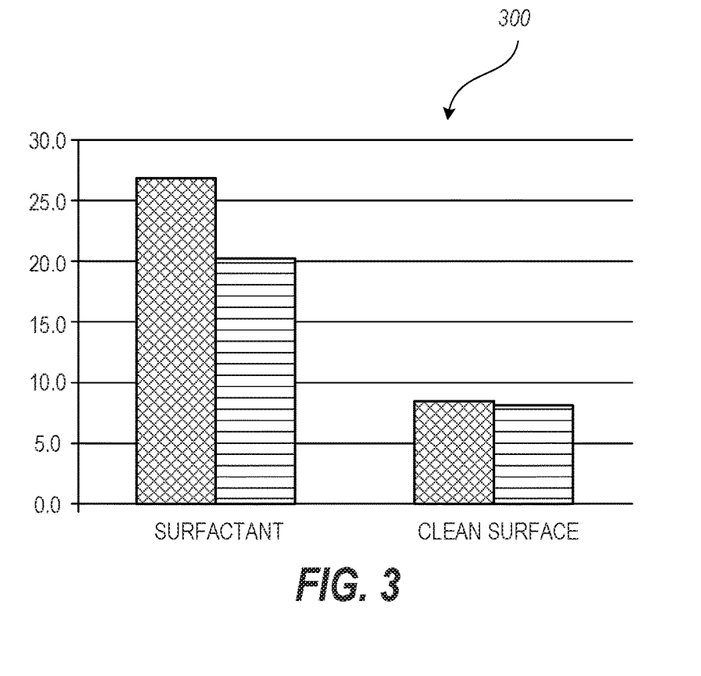
FIG. 3 illustrates a bar graph of empirical results of water contact angles determined on clean and surfactant covered aluminum surfaces 300 ms after water deposition and 600 ms after deposition using the testing device of FIG. 1, according to one or more embodiments.

In one example, aluminum coupons were prepared by a solvent wipe using isopropanol and paper towels. One set of these coupons was then cleaned using an atmospheric pressure plasma with air as the process gas (RD1000, Plasmatreat, Inc.). Another set of these coupons was contaminated by wiping with a thin film of an industrial surfactant from an automated parts washer (Oxynol, Corrosion Solutions & Fluid Design, LLC). Water contact angles were obtained using ballistically deposited water drops at two time intervals: 300 ms and again at 600 ms after deposition of the water drop. FIG. 3 shows the results 300. In this example the clean surfaces showed an average contact angle change of 0.6° while the surfactant contaminated surfaces showed an average contact angle change of 6.6°. Thus, discrimination between a clean surface and surfactant contaminated surface is readily accomplished by comparison of the evolution of the contact angle over a short period of time after deposition of the probe fluid drop, in this case 300 ms. The exact time interval is not critical, as similar conclusions could be reached if the contact angles were to be compared after a shorter or longer time interval after deposition.

Figure 4:
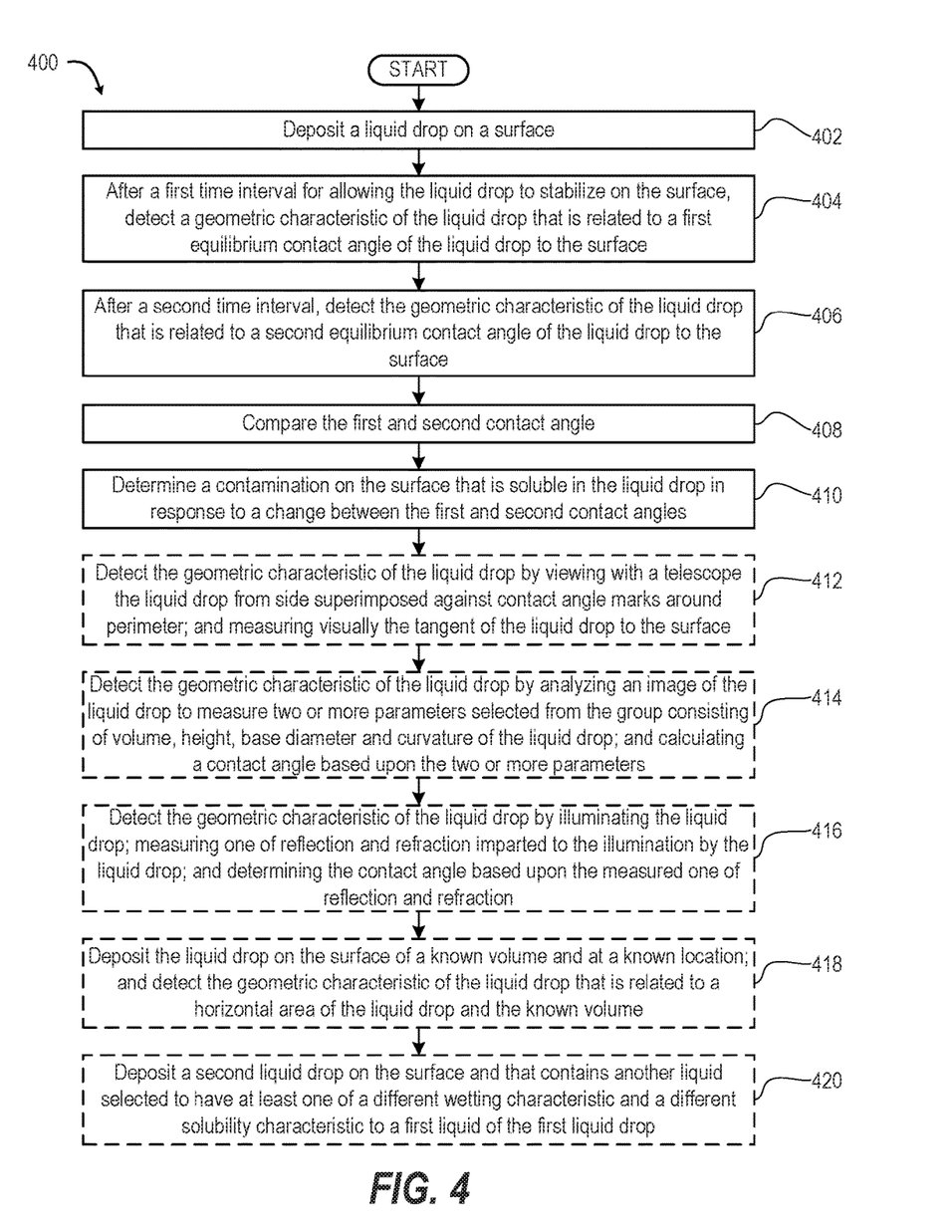
FIG. 4 illustrates a flow diagram of a method of determining the presence of a soluble substance on a surface that change a surface energy characteristic of a liquid drop over time, according to one or more embodiments.

FIG. 4 illustrates a method 400 of determining the presence of substances on a surface. In one or more embodiments, the method 400 includes depositing a liquid drop on a surface (block 402). The method 400 includes, after a first time interval for allowing the liquid drop to stabilize on the surface, detecting a geometric characteristic of the liquid drop that is related to a first equilibrium contact angle of the liquid drop to the surface (block 404). The method 400 includes, after a second time interval, detecting the geometric characteristic of the liquid drop that is related to a second equilibrium contact angle of the liquid drop to the surface (block 406). The method 400 includes comparing the first and second contact angle (block 408). The method 400 includes determining a contamination on the surface that is soluble in the liquid drop in response to a change between the first and second contact angles (block 410).

In one embodiment, the method 400 includes detecting the geometric characteristic of the liquid drop by viewing with a telescope the liquid drop from side superimposed against contact angle marks around perimeter; and measuring visually the tangent of the liquid drop to the surface (block 412).

In one embodiment, the method 400 includes detecting the geometric characteristic of the liquid drop by analyzing an image of the liquid drop to measure two or more parameters selected from the group consisting of volume, height, base diameter and curvature of the liquid drop; and calculating a contact angle based upon the two or more parameters (block 414).

In one embodiment, the method 400 includes detecting the geometric characteristic of the liquid drop by illuminating the liquid drop; measuring one of reflection and refraction imparted to the illumination by the liquid drop; and determining the contact angle based upon the measured one of reflection and refraction (block 416).

In one embodiment, the method 400 includes depositing the liquid drop on the surface of a known volume and at a known location; and detecting the geometric characteristic of the liquid drop that is related to a horizontal area of the liquid drop and the known volume (block 418).

In one embodiment, the method 400 includes depositing a second liquid drop on the surface and that contains another liquid selected to have at least one of a different wetting characteristic and a different solubility characteristic to a first liquid of the first liquid drop (block 420).

Figure 5:
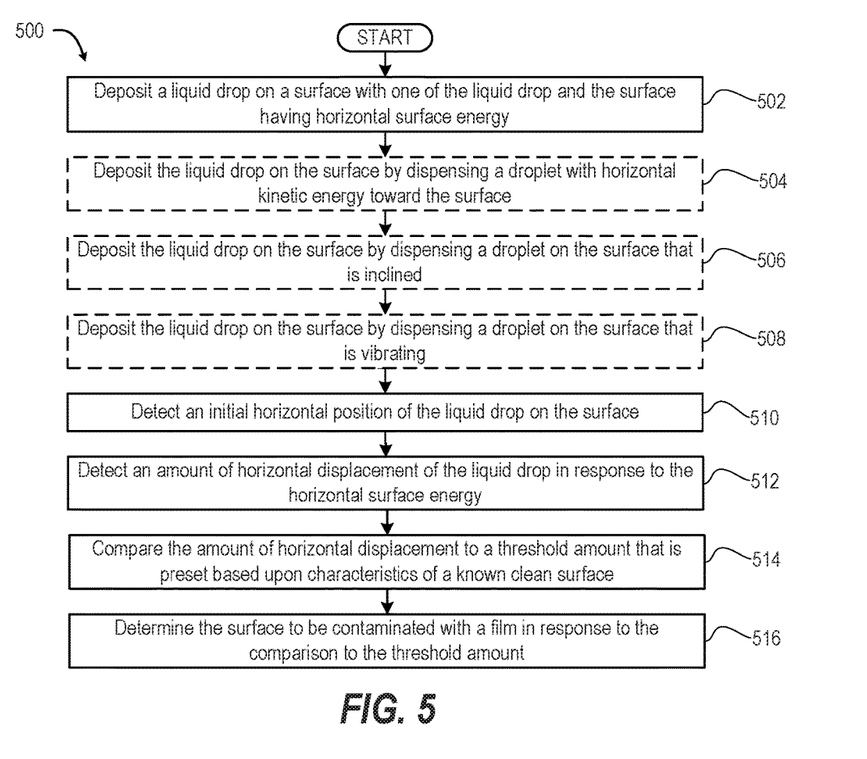
FIG. 5 illustrates a flow diagram of a method of determining the presence of insoluble substances on a surface that change a wetting characteristic of the surface, according to one or more embodiments.

FIG. 5 illustrates a method 500 of determining the presence of substances on a surface. According to one or more embodiments, the method 500 includes depositing a liquid drop on a surface with one of the liquid drop and the surface having horizontal surface energy (block 502). In one embodiment, the method 500 includes depositing the liquid drop on the surface by dispensing a droplet with horizontal kinetic energy toward the surface (block 504). In one embodiment, the method 500 includes depositing the liquid drop on the surface by dispensing a droplet on the surface that is inclined (block 506). In one embodiment, the method 500 includes depositing the liquid drop on the surface by dispensing a droplet on the surface that is vibrating (block 508). The method 500 includes detecting an initial horizontal position of the liquid drop on the surface (block 510). The method 500 includes detecting an amount of horizontal displacement of the liquid drop in response to the horizontal surface energy (block 512). The method 500 includes comparing the amount of horizontal displacement to a threshold amount that is preset based upon characteristics of a known clean surface (block 514). The method 500 includes determining the surface to be contaminated with a film in response to the comparison to the threshold amount (block 516).

By virtue of the foregoing, the present innovation provides in various aspect the following: a housing, a liquid dispensing component, and a data generating component, wherein the liquid dispensing component is configured to deposit a volume of a liquid on the surface of the material; wherein the position determining component is configured to convey information about the position of the device relative to the volume of liquid on the surface of the liquid; wherein the data generating component is configured to obtain information about the geometrical features of the volume of the liquid on the surface of the material and wherein the device is configured to determine changes in one or more geometrical features.

In one embodiment, the device determines changes in one or more geometrical features as a function of time after contact of the liquid is established with the surface. In one embodiment, the device further comprises a set of rules for interpreting the data obtained by the device in claim 1 to determine characteristics of the surface or a contaminant present on the surface.

In one embodiment, the present disclosure provides a method for determining the presence of substances on surfaces comprising the steps of: depositing a liquid in a manner whereby the volume of the drop is increased through stepwise addition of smaller drops; whereby each increment of volume growth causes the perimeter of the drop to advance across the surface; and whereby the incremental volume elements sufficient energy is imparted to the growing drop such that the drop perimeter expands beyond its equilibrium diameter for that volume; whereby the drop perimeter will tend to contract between volume additions as the excess energy is dissipated, and determining changes in one or more geometrical features. In one embodiment, the method further comprises determining changes to one or more geometrical features as a function of time after contact of the liquid is established with the surface. In a particular aspect, the method further comprises using a set of rules for interpreting the data obtained by the device to determine characteristics of the surface or a contaminant present on the surface.

In one embodiment, a testing device includes a housing 120, a liquid dispensing component, position determining component and a data generating component. The liquid dispensing component, which is also referred to herein as the liquid dispenser, is configured to deposit a volume of a liquid on the surface of a substrate material. The position determining component is configured to obtain information about the position of the device relative to the volume of liquid on the surface. The data generating component, also referred to herein as the data generator, is configured to obtain information about the geometry of the volume of the liquid on the surface of the material. All of these components may be incorporated into a single, handheld device that would be extremely convenient for use in a manufacturing environment on a variety surfaces and structures in a variety of orientations.

All publications, patents and patent applications cited herein, whether supra or infra, are hereby incorporated by reference in their entirety to the same extent as if each individual publication, patent or patent application was specifically and individually indicated as incorporated by reference.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A testing device for determining the presence of substances on a surface, the testing device comprising:
a sensor positioned at a known vantage point to a surface;

a liquid dispenser to ballistically dispense one or more pulses of liquid to deposit a liquid drop on the surface;
a data generator to:
after a first time interval, detect via the sensor a geometric characteristic of the liquid drop that is related to a contact angle of the liquid drop to the surface corresponding to the first time interval;
after a second time interval, detect via the sensor a geometric characteristic of the liquid drop that is related to a second contact angle of the liquid drop to the surface corresponding to the second time interval;
compare the first and second geometric characteristics; and
determine a substance on the surface that is capable of interacting with the liquid through dissolution or some other interaction based on a change between the first and second geometric characteristics.

2. The testing device of claim 1, wherein the data generator is further to detect via the sensor the geometric characteristic of the liquid drop by: viewing the liquid drop from side to determine the tangent of the liquid drop to the surface.

3. The testing device of claim 1, wherein the data generator is further to detect via the sensor the geometric characteristic of the liquid drop by:
analyzing an image of the liquid drop to measure one or more parameters selected from the group consisting of volume, height, base diameter, cross sectional area, and curvature of the liquid drop; and
calculating a contact angle based upon the two or more parameters.

4. The testing device of claim 1, further comprising an illuminator, wherein the data generator is further to detect via the sensor the geometric characteristic of the liquid drop by:
illuminating the liquid drop with the illuminator; and
measuring one of reflection and refraction imparted to the illumination by the liquid drop;
determining the contact angle based upon the measured one of reflection and refraction.

5. The testing device of claim 1, wherein:
the liquid dispenser is further to deposit the liquid drop of known volume on the surface and at a known location; and
the data generator is further to detect the geometric characteristic of the liquid drop that is related to the contact area or diameter of the liquid drop and the known volume.

6. The testing device of claim 1, wherein:
the liquid dispenser is further to deposit a liquid drop on a surface with one of the liquid drop and the surface having kinetic energy parallel to the plane of the contact; and
the data generator is further to:
detect via the sensor an initial position of the liquid drop on the surface;
detect via the sensor a stopping position of the liquid drop on the surface;
determine an amount of displacement of the liquid drop in the plane of the surface in response to the kinetic energy parallel to the plane of contact based on the initial position and the stopping position;
compare the amount of the displacement in the plane of contact to a threshold amount that is preset based upon characteristics of a known surface; and
determine the surface to include a substance in response to the comparison to the threshold amount.

7. The testing device of claim 6, wherein the liquid dispenser comprises: (i) an orifice that is sized to create droplets of a selected volume; and (ii) a pump that dispenses more than one droplet at a selected velocity from the orifice to create the liquid drop with kinetic energy parallel to the plane of contact toward the surface.

8. The testing device of claim 6, wherein the surface is inclined.

9. The testing device of claim 6, wherein the surface is vibrating.

10. The testing device of claim 1, further comprising:
a source of a second liquid that is selectable to reevaluate multiple component vector quantities of the surface for obtaining a more accurate surface energy calculation.

11. The testing device of claim 1, wherein the sensor is positioned at the known vantage point comprising a known distance and known angle to the surface.

12. The testing device of claim 1, wherein the data generator determines the substance on the surface that is capable of interacting with the liquid through dissolution or some other interaction causing the change between the first and second geometric characteristics comprising respective contact angles.

13. The testing device of claim 1, further comprising:
a source of a second liquid that is selectable for deposition on the surface, wherein a surface energy calculation is obtainable from contact angle measurements for the first and second liquids.

14. A method of determining the presence of substances on a surface, the method comprising:
ballistically dispensing one or more pulses of liquid to deposit a liquid drop on a surface;
after a first time interval, detect via the sensor a geometric characteristic of the liquid drop that is related to a contact angle of the liquid drop to the surface corresponding to the first time interval;
after a second time interval, detect via the imaging detector the geometric characteristic of the liquid drop that is related to a second contact angle of the liquid drop to the surface corresponding to the second time interval;
compare the first and second contact angle; and
determine a substance on the surface that is capable of interacting with the liquid through dissolution or some other interaction in response to a change between the first and second contact angles.

15. The method of claim 14, wherein detecting the geometric characteristic of the liquid drop further comprises:
viewing the liquid drop from side to determine the tangent of the liquid drop to the surface.

16. The method of claim 14, wherein detecting the geometric characteristic of the liquid drop further comprises:
analyzing an image of the liquid drop to measure two or more parameters selected from the group consisting of volume, height, base diameter and curvature of the liquid drop; and
calculating a contact angle based upon the two or more parameters.

17. The method of claim 14, wherein detecting the geometric characteristic of the liquid drop further comprises:
illuminating the liquid drop;
measuring one of reflection and refraction imparted to the illumination by the liquid drop; and
determining the contact angle based upon the measured one of reflection and refraction.

18. The method of claim 14, further comprising: depositing the liquid drop on the surface of a known volume and at a known location; and detecting the geometric characteristic of the liquid drop that is related to a horizontal area of the liquid drop and the known volume.

19. The method of claim 14, further comprising: depositing a second liquid drop on the surface and that contains another liquid selected to have at least one of a different wetting characteristic and a different solubility characteristic to a first liquid of the first liquid drop.

20. A method of determining the presence of substances on a surface, the method comprising:

depositing a liquid drop on a surface with one of the liquid drop and the surface having kinetic energy parallel to the plane of the surface;

detecting an initial position of the liquid drop on the surface;

detecting a stopping position of the liquid drop on the surface;

determining an amount of displacement of the liquid drop parallel to the plane of the surface in response to a change in the surface energy of the substrate, a change in the surface tension of the liquid or both; wherein the amount of displacement is based on the initial position and the stopping position;

comparing the amount of displacement to a threshold amount that is preset based upon characteristics of a known clean surface; and determining the surface to be contaminated with a film in response to the comparison to the threshold amount.

21. The method of claim 20, wherein the depositing the liquid drop on the surface comprises dispensing a droplet with kinetic energy parallel to the plane of the surface toward the surface using a liquid dispenser comprising: (i) an orifice that is sized to create droplets of a selected volume; and (ii) a peristaltic pump that dispenses more than one droplet at a selected velocity.

22. The method of claim 20, wherein the depositing the liquid drop on the surface comprises dispensing a droplet on the surface that is inclined at an angle less than an angle sufficient for the liquid drop to continue moving due to gravity.

23. The method of claim 20, wherein the depositing the liquid drop on the surface comprises dispensing a droplet on the surface that is vibrating.

* * * * *